United States Patent [19]

Thomas, III et al.

[11] Patent Number: 4,911,170

[45] Date of Patent: Mar. 27, 1990

[54] HIGH FREQUENCY FOCUSED ULTRASONIC TRANSDUCER FOR INVASIVE TISSUE CHARACTERIZATION

[75] Inventors: Lewis J. Thomas, III, Schenectady; Robert S. Gilmore, Burnt Hills; Casmir R. Trzaskos, Amsterdam, all of N.Y.

[73] Assignee: General Electric Company, Schenectady, N.Y.

[21] Appl. No.: 235,067

[22] Filed: Aug. 22, 1988

[51] Int. Cl.$^4$ ............................................. A61B 8/00
[52] U.S. Cl. ........................... 128/662.06; 128/660.03
[58] Field of Search ..................... 128/660.03, 662.06, 128/305; 604/100

[56] References Cited

U.S. PATENT DOCUMENTS

| | | | |
|---|---|---|---|
| 4,546,771 | 10/1985 | Eggleton et al. | 128/662.05 X |
| 4,572,201 | 2/1986 | Kondo et al. | 128/662.06 |
| 4,576,177 | 3/1986 | Webster, Jr. | 128/660.03 |
| 4,587,972 | 5/1986 | Morantte, Jr. | 128/660.03 |
| 4,758,223 | 7/1988 | Rydell | 604/98 |
| 4,760,304 | 7/1988 | Oliver | 310/335 |
| 4,794,931 | 1/1989 | Yock | 128/660.03 |
| 4,821,731 | 4/1989 | Martinelli et al. | 128/660.03 X |

FOREIGN PATENT DOCUMENTS 0114994  7/1984  Japan .............................. 128/662.06

OTHER PUBLICATIONS

R. S. Gilmore et al., "Acoustic Microscopy from 10 to 100 MHz for Industrial Applications", Phil. Trans. R. Soc. Lond., A320, 215-235 (1986).

Primary Examiner—Francis Jaworski
Attorney, Agent, or Firm—Henry I. Steckler; James C. Davis, Jr.; Paul R. Webb, II

[57] ABSTRACT

A broadband 25 to 50 MHz spherically focused ultrasonic transducer is placed on the tip of a catheter such that ultrasonic images of arteries and plaque are produced by introducing the catheter into arteries of patients. The high frequency transducer has thin piezoelectric polymer film as the transducing element and is adhered to a depression in the reduced cross section catheter tip. A coaxial cable in the catheter connects the transducer to an external signal source and a display for the received signals. The diagnosis and characterization of arterial disease is most often coupled with a therapeutic technique such as balloon angioplasty.

10 Claims, 4 Drawing Sheets

HIGH FREQUENCY FOCUSED ULTRASONIC TRANSDUCER FOR INVASIVE TISSUE CHARACTERIZATION

BACKGROUND OF THE INVENTION

This invention relates to an ultrasonic transducer on medical apparatus that is introduced into the body and especially to a method of characterizing arterial disease by generating ultrasound from within the artery.

Atherosclerosis, hardening of the arteries, afflicts most people living in developed countries. Coronary artery disease is the primary cause of ischemic heart disease, which is responsible for more deaths in this country than any other disease. Treatment of artherosclerosis currently relies on considerable guess work by the physician. Some forms of plaque, which are calcified lesions on arteries, may be effectively treated by drugs while others require surgery. Also, approximately 30% of patients who undergo balloon angioplasty for opening of occluded arteries, the major cause of heart attacks, redevelop the occlusion within three months. In order to select the proper course of treatment and to assess the success of treatment, some means to differentiate types of plaques is needed.

Most work attempting to characterize artery disease has used ultrasound at the relatively low frequencies of 5 to 15 MHz. This is because the transducers were placed on the surface of the skin, and therefore the ultrasound has to penetrate considerable distance before the artery was reached. Because of the high acoustic attenuation at the higher frequencies of 25 to 50 MHz, these frequencies could not be used to penetrate deep enough into the body to characterize arteries. Even carotid arteries which lie very close to the skin in the neck are typically examined with 15 MHz ultrasound. Due to the long wavelengths and broad beamwidths of these systems little success has been achieved in differentiating various types of atherosclerotic plaques even in relatively accessible arteries such as the carotid. This work is described at length in the medical literature.

Broadband high frequency (25 to 50 MHz) focused transducers have been available for many years, and an ultrasonic microscope represents one of the most significant applications of these transducers to nondestructive testing. Refer for instance to "Acoustic Microscopy From 10 to 100 MHz for Industrial Applications", R. S. Gilmore et al., Phil. Trans. R. Soc. Lond. A320, 215-235 (1986). These systems are inappropriate for introduction into arteries because of the size of the transducers, typically several inches. Measurements in such an ultrasonic microscope on excised artery specimens using a broadband 50 MHz transducer focused with an F/2 lens indicate that the system can differentiate between normal artery and fatty plaques, an early stage of atherosclerosis not normally detectable.

The ultrasonic transducers of this invention may be fabricated from thin piezoelectric polymer film such as PVDF (poly vinylidene di fluoride). High frequence transducing elements of this material are described in patent 4,760,304, D. W. Oliver, "Dark Field Coaxial Ultrasonic Transducer" and allowed divisional application S.N. 126,325, filed Nov. 30, 1987, "Method of Fabricating Dark Field Coaxial Ultrasonic Transducer" now U.S. Pat. No. 4,787,126.

SUMMARY OF THE INVENTION

An object of the invention is to provide a device for improved characterization of various types of arterial and heart disease by introducing a broadband high frequency ultrasonic transducer into the artery or heart and examining backscattered ultrasonic signals.

Another object is the provision of an ultrasonic transducer on the tip of a catheter for improved differentiation and measurement of atherosclerotic plaque.

Yet another object is to coordinate and couple the characterization of vascular disease by in vivo ultrasound examination with the treatment of the diseased tissue.

One aspect of the invention is medical apparatus for invasive ultrasonic tissue characterization comprising an elongated flexible catheter to be inserted into the body which has a broadband high frequency focused ultrasonic transducer mounted on the tip of the catheter, which may have a reduced cross section, to transmit ultrasound into the body and receive echoes from body structures and diseased tissue. An electrical cable inside the catheter is connected to the transducer and exteriorly to other components of the imaging system. The latter is comprised of means to pulse the transducer to display received signals. A high frequency, 25 MHz to 50 Mhz, spherically focused transducer has a thin piezoelectric polymer film transducing element such as PVDF which is adhered to a spherically shaped depression in the end of the catheter.

The preferred embodiment is an ultrasonic tipped catheter to be inserted into and produce images of an artery. The catheter tip is approximately hemispherical and the high frequency spherically focused transducer is mounted on the tip to transmit ultrasound approximately perpendicular to the longitudinal axis of the catheter so as to be incident on a wall of the artery and detect ultrasound backscattered from the wall and any plaque in the artery. The catheter may have means to treat the plaque, such as an inflatable balloon to perform balloon angioplasty. This device may be used to determine treatment strategies and to ascertain the efficacy of the treatment.

Another aspect of the invention is a method of characterizing arteries in vivo. An ultrasonic tipped catheter as already described is inserted into the artery, and the transducer is pulsed, generates ultrasound, and receives ultrasound backscattered from an artery wall and any plaque in the artery. The final step is imaging the backscattered signals in order to characterize the arterial disease. A further feature is that ultrasonic imaging of the artery may be coupled with balloon angioplasty or another therapeutic technique.

DETAILED DESCRIPTION OF THE INVENTION

Many different types of catheters are used to study different parts of the body. For examining large arteries and the inside of the heart, the catheter may be as simple as a relatively large piece of plastic tube with a 2.5 to 3 mm diameter. For measurements in the coronary arteries smaller catheters having a diameter of 1.2 to 1.5 mm which have steerable guide wires are used. This description will discuss an ultrasonic catheter which can be used in coronary arteries; however, with the removal of the guide wire and increases in the size of the catheter, this design could be adapted for use in larger arteries or the heart.

Figure 2:
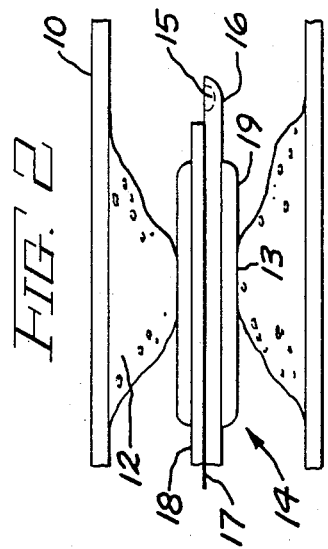
FIG. 2 is a longitudinal cross section through the artery and a catheter having an ultrasonic transducer on the tip to characterize arterial disease and a balloon to treat the disease.
Figure 1:
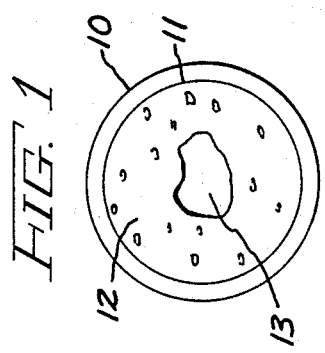
FIG. 1 is a cross section of a human artery illustrating deposits of a plaque.

In FIG. 1 is shown a diseased coronary artery which has a 3 millimeter diameter. The outer and inner walls are seen at 10 and 11 and the fatty plaque 12 is of sufficient extent that the opening 13 in the artery may have a diameter as small as 1 mm. In FIG. 2, an ultrasonic tipped catheter 14 is introduced into the artery and remaining opening 13 to produce ultrasonic images of the artery and characterize arterial disease. The catheter itself may be conventional except that the tip is partly cut away, and a broadband high frequency focused ultrasonic transducer 15 is mounted in the reduced cross section tip portion 16. This catheter has a guide wire 17 running longitudinally through the center of the tubular catheter body 18; this wire has a flexible tip and is used to steer the catheter into the appropriate location in the artery, and is then withdrawn when the ultrasonic measurements are made. An inflatable balloon 19 on a forward section of the catheter is used to perform balloon angioplasty and treat the fatty plaque. The catheter may instead have means to perform another type of therapy such as laser angioplasty. Most commonly the ultrasonic diagnostic and characterization technique is coupled with a therapeutic technique such as balloon or laser angioplasty.

The ultrasonic transducer 15 is preferably a 25 MHz to 50 MHz, spherically focused device that transmits ultrasound to be incident on the artery walls 10 and 11 and detects ultrasound backscattered from these walls and any plaque 12 in the artery. The ultrasound examination has three functions, the location, the diagnosis, and characterization of arterial disease. As the ultrasonic catheter is moved through the artery, the ultrasonic measurements serve to locate the plaque precisely and the thickness of plaque may be measured before and after a treatment such as balloon angioplasty. The characteristics of the plaque are determined, specifically is it a type than can be treated by balloon angioplasty and if another type of treatment such as bypass surgery is needed.

Figure 3:
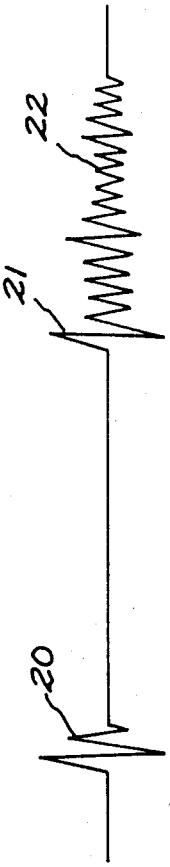
FIGS. 3 and 4 show transmitted and received signals from a healthy artery and a diseased artery having fatty plaque deposits.
Figure 4:
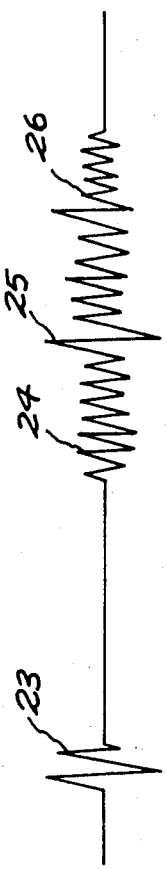

Radio frequency waveforms recorded from normal and fatty regions of the artery are shown in FIGS. 3 and 4. When there is normal tissue the large amplitude transmitted signal 20 is followed by a large amplitude received signal 21 representing ultrasound backscattered from the artery wall and a short period of lower amplitude echo signals 22. The acoustic signal resulting from a diseased artery having fatty plaque deposits is easily distinguished. The transmitted signal 23 is followed by lower amplitude signals 24 resulting from ultrasound backscattered by the fatty plaque. The larger voltage signal 25 and lower amplitude echo signal voltages 26 representing reflections from the wall and subsequent echoes are as before. Some plaque may be more rather than less reflecting; in this case the echo from the plaque may be larger than the wall echo. These are one-dimensional images of the echoes from one point in the artery such as might be displayed on an oscilloscope. When the entire catheter is rotated or only the tip, this yields a two-dimensional, B-scan display.

Figure 5:
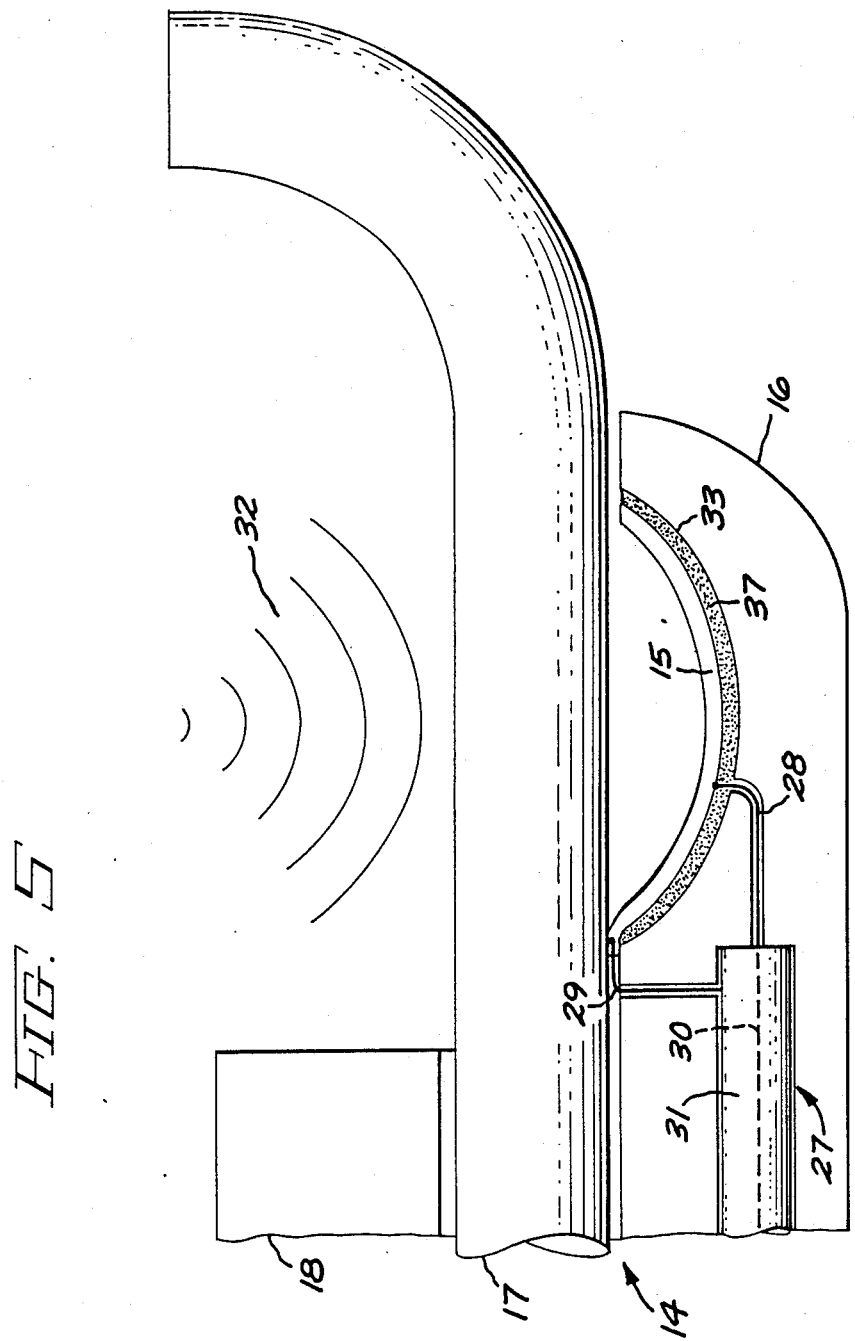
FIG. 5 is a longitudinal cross section of the catheter tip showing the ultrasonic transducer and a guide wire that is retracted to make acoustic measurements.

In FIG. 5 there is shown a longitudinal cross section of the tip of the ultrasonic catheter 14. The body 18 of the catheter is usually made of a flexible, inert plastic. A guide wire 17 with a flexible spring-like tip runs down the center of the catheter. Electrical signals are transmitted to and received from ultrasonic transducer 15 via a coaxial electrical cable 27 running the length of the catheter. The heart of the system is the ultrasonic transducer 15 itself which suitably has a piezoelectric polymer as the transducing element. Gold or aluminum electrodes are applied to the film to provide electrical connections to the cable. Wires 28 and 29 connect the two electrodes to the center and outer conductors 30 and 31 of the cable. With the guide wire 17 retracted, pulsing the transducer 15 generates a focused ultrasonic field 32 that propagates toward the artery wall in a direction approximately perpendicular to the longitudinal axis of the catheter.

Figure 6:
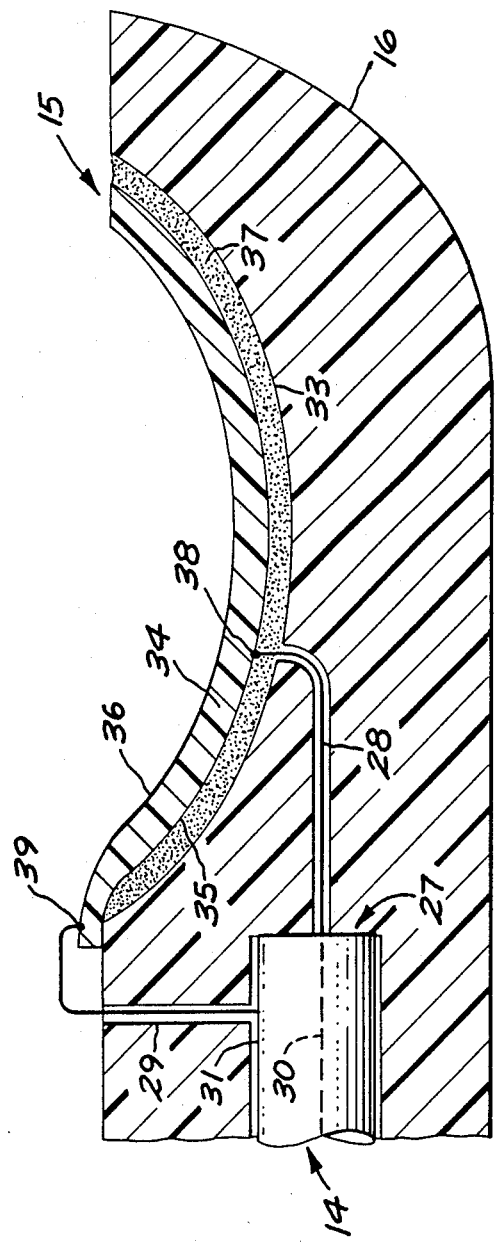
FIG. 6 is a longitudinal cross section to a larger scale of a portion of the catheter tip and the high frequency PVDF film ultrasonic transducer.

The reduced cross section, approximately hemispherical tip portion 16 of ultrasonic catheter 14, and the ultrasonic transducer 15 and its connections to coaxial cable 27 are shown to an enlarged scale in FIG. 6. The preferred piezoelectric polymer is PVDF (poly vinylidene difluoride). By using very thin PVDF films, 9 microns or less in thickness, good broadband high frequency transducers may be realized and, since the PVDF film is thin, the material may be focused simply by attaching the PVDF to an appropriately shaped support. In order to produce the correct geometry for focusing the ultrasonic field at the artery wall, a spherically shaped depression 33 is machined in the center tip. The high frequency spherically focused transducer 15 is fabricated by laying over the cavity a circular disk of the PVDF film 34 which has gold electrodes 35 and 36 on either surface, and pressing the disk into the cavity with an appropriately sized ball. The transducer is adhered to the catheter tip by a layer 37 of non-conductive epoxy. Small dots of conductive epoxy 38 and 39 serve to attach the wires 28 and 29 to the inner and outer electrodes 35 and 36. The diameter of the 25 MHz to 50 MHz broadband spherically focused transducer 15 can be approximately equal to the external diameter of the catheter. The diameter may thus be as small as 1 mm to 3 mm.

Figure 7:
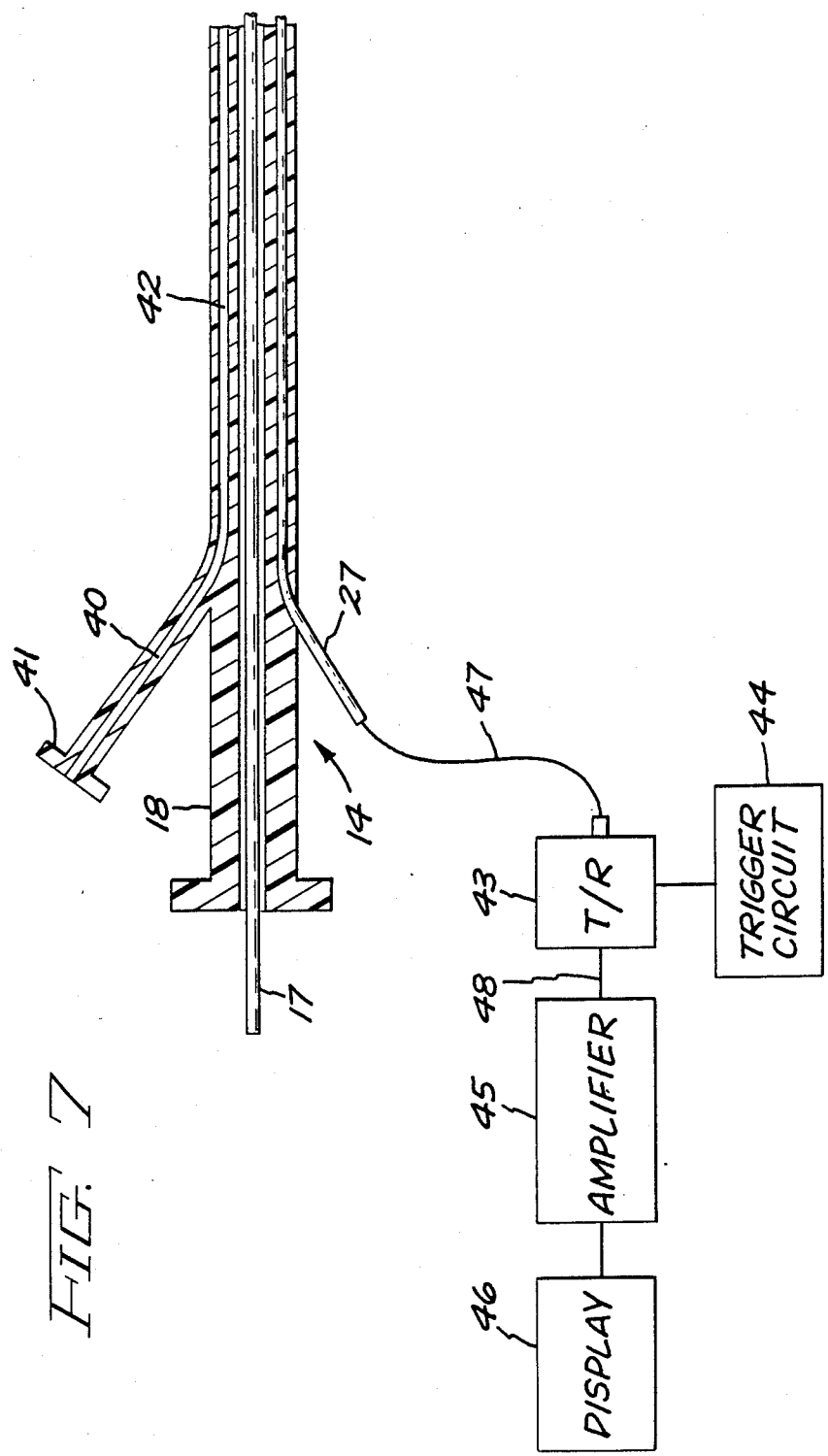
FIG. 7 shows the other end of the catheter and a block diagram of the ultrasonic imaging system.

FIG. 7 is a diagram of the other end of the ultrasonic tipped catheter 14 which is external to the body of the patient. The ultrasonic imaging system itself, other than the high frequency transducer, may be conventional and the external components are illustrated. A tube 40 is provided for radio-opaque dye to inflate the balloon 19. This tube has a lock structure 41 for attachment to a syringe and exits into a small channel 42 that extends most of the length of the catheter to the balloon 19 (FIG. 2) near the tip. The electrical coaxial cable 27 exits the catheter body 18 near the end of the catheter. The imaging system components include a transmit/-receive unit 43, a trigger circuit 44 to time the generation of RF pulses, an amplifier 45, and a display device 46. Coaxial cable 27 can be a 50 ohm transmission line, and 50 ohm cables 47 and 48 interconnect the transmit/-receive unit 43 with the coaxial cable and with amplifier 45. Display 46 may be a simple oscilloscope, a television monitor, or a computer system.

An ultrasonic tipped catheter has been described such that ultrasonic images of arteries are produced by introducing a transducer into the arteries of patients. This new arterial disease characterization apparatus may be used both to determine appropriate treatment strategies and to ascertain the efficacy of the treatment. Other applications of the invention are the diagnosis and characterization of various types of vascular and heart disease. The latter includes characterization of myocardium as a replacement for endocardial biopsy for determination of global heart disease such as cardiomyopathy and heart rejection after a heart transplant.

While the invention has been particularly shown and described with reference to preferred embodiments thereof, it will be understood by those skilled in the art that various changes in form and details may be made without departing from the spirit and scope of the invention as defined in the appended claims.

What is claimed is:

1. Medical apparatus for invasive ultrasonic tissue characterization comprising:
    an elongated flexible catheter to be inserted into a human body and which has means thereon to treat diseased tissue;
    a broadband 25 to 50 megahertz focused ultrasonic transducer mounted on a tip portion of said catheter to transmit ultrasound into the body and receive echoes from body structures and said diseased tissue, and an electrical cable in said catheter connecting to said transducer and to an external imaging system;
    said imaging system having means to pulse said transducer and display signals, and wherein said transducer has a piezoelectric poly vinylidene di fluoride polymer film transducing element having a maximum thickness of 9 microns and is spherically focussed.

2. The apparatus of claim 1 wherein the tip of the catheter has an approximately hemispherical cross section and a spherically shaped depression in which is adhered said transducer.

3. The apparatus of claim 1 wherein said means to treat diseased tissue is an inflatable balloon to perform balloon angioplasty.

4. Medical apparatus for invasive ultrasonic tissue characterization comprising:
    an elongated flexible catheter to be inserted into a human artery, said catheter having a longitudinal axis and a reduced cross section top portion;
    a broadband high frequency focused ultrasonic transducer mounted in said tip portion to transmit ultrasound approximately perpendicular to the longitudinal axis of said catheter to be incident on a wall of said artery and detect ultrasound backscattered from said wall and any plaque in said artery, and an electrical coaxial cable inside said catheter connecting to said transducer and to an external imaging system;
    said imaging system having means to pulse said transducer and display signals, and wherein said transducer is a spherically focused device having a piezoelectric poly vinylidene di fluoride polymer film with a maximum thickness of 9 microns as the transducing element.

5. The apparatus of claim 4 wherein said transducer is a 25 to 50 megahertz transducer.

6. The apparatus of claim 4 wherein the tip portion of said catheter has a circular hollowed out depression in which is adhered said transducer which is a spherically focused device.

7. The apparatus of claim 6 wherein said transducer is a 25 to 50 megahertz transducer.

8. A method of characterizing arteries in vivo comprising:
    inserting into a human artery a catheter which has at the tip a broadband 25 to 50 megahertz focused poly vinylidene di fluoride polymer film with with a maximum thickness of 9 microns ultrasonic transducer;
    pulsing said transducer and generating ultrasound and receiving backscattered signals from a wall of said artery and any plaque in said artery; and
    imaging said backscattered signals in order to characterize arterial disease.

9. The method of claim 8 wherein said catheter has means to treat the arterial disease and said imaging is coupled with operation of said means.

10. The method of claim 8 wherein said catheter has a balloon to perform angioplasty and said imaging is coupled with operation of said balloon to treat the arterial disease.

* * * * *